US008242088B2

(12) United States Patent
Joliot et al.

(10) Patent No.: US 8,242,088 B2
(45) Date of Patent: Aug. 14, 2012

(54) CARRIER VECTORS THROUGH AN EPITHELIUM WITH TIGHT JUNCTIONS

(75) Inventors: Alain Joliot, Paris (FR); Edmond Dupont, Paris (FR); Alain Prochiantz, Paris (FR)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 10/432,291

(22) PCT Filed: Nov. 20, 2001

(86) PCT No.: PCT/FR01/03631
§ 371 (c)(1),
(2), (4) Date: May 20, 2003

(87) PCT Pub. No.: WO02/39947
PCT Pub. Date: May 20, 2002

(65) Prior Publication Data
US 2004/0029281 A1 Feb. 12, 2004

(30) Foreign Application Priority Data
Nov. 20, 2000 (FR) ................................ 00 14945

(51) Int. Cl.
*C12N 15/11* (2006.01)
*A61K 48/00* (2006.01)
*A61K 38/00* (2006.01)
(52) U.S. Cl. .......................................... 514/44; 514/1.1
(58) Field of Classification Search ............... 435/320.1; 530/350; 514/44, 1.1
See application file for complete search history.

(56) References Cited

U.S. PATENT DOCUMENTS

| 6,472,176 | B2 * | 10/2002 | Kovesdi et al. | ............... | 435/69.1 |
| 6,773,920 | B1 * | 8/2004 | Dalby et al. | ................... | 435/462 |
| 2002/0110869 | A1 * | 8/2002 | Kovesdi et al. | ............... | 435/69.7 |

FOREIGN PATENT DOCUMENTS

| WO | WO 99/05302 | 2/1999 |
| WO | WO 00/29427 | 5/2000 |
| WO | WO 00/58488 | 10/2000 |
| WO | WO 00/62067 A1 | 10/2000 |
| WO | WO 01/13957 A2 | 3/2001 |
| WO | WO 01/38547 A2 | 5/2001 |

OTHER PUBLICATIONS

Hassen, et al. (1999) The Plant Journal, 20(6): 695-705.*
Schwarze et al., Protein transduction: unrestricted delivery into all cells? Trends Cell Biol. 10(7): 290-5, 2000.*
Gloor et al., Molecular and cellular permeability control at the blood-brain barrier. Brain Res Brain Res Rev. 36(2-3): 258-64, 2001.*
Joliot et al., Transduction peptides: from technology to physiology. Nat Cell Biol. 6(3): 189-196, 2004.*
Pouton and Seymour, Key issues in non-viral gene delivery, Adv Drug Deliv Rev. 46(1-3): 187-203, 2001.*
Johnson-Saliba et al. Gene therapy: optimizing DNA delivery to the nucleus. Curr Drug Targets. 2(4): 371-99, 2001.*
Read et al., Barriers to gene delivery using synthetic vectors, Adv Genet. 53: 19-46, 2005.*
Dobson, Gene therapy progress and prospects: magnetic nanoparticle-based gene delivery. Gene Ther. 13(4): 283-7, 2006.*
Zegers et al., Mechanisms and functional features of polarized membrane traffic in epithelial and hepatic cells, Biochem J. 336 (Pt 2):257-69, 1998.*
Schwarze et al. Protein transduction: unrestricted delivery into all cells? Trends Pharmacol Sci. 21(2):45-8, 2000.*
Pooga et al., Cell penetrating PNA constructs regulate galanin receptor levels and modify pain transmission in vivo, Nat Biotechnol. 16(9):857-61, 1998.*
Maizel et al. A short region of its homeodomain is necessary for engrailed nuclear export and secretion, Development, 126(14):3183-90, 1999.*
Shaw et al., Migration of intestinal intraepithelial lymphocytes into a polarized epithelial monolayer, Am J Physiol. 275(3 Pt 1):G584-91, 1998.*
The ARTFL project: French-English Dictionary, p. 1, 2005.*
D. Derossi et al., "Trojan Peptides: The Penetratin System for Intracellular Delivery", Trends in Cell Biology, vol. 8, Feb. 1998, pp. 84-87.
S. R. Schwarze et al., "In Vivo Protein Transduction: Delivery of a Biologically Active Protein into the Mouse", Science, American Association for the Advancement of Science, vol. 285, No. 5433, Sep. 3, 1999, pp. 1569-1572.
E. Bellet-Amalric et al., "Interaction of the Third Helix of Antennapedia Homeodomain and a Phospholipid Monolayer, Studied by Ellipsometry and PM-IRRAS at the Air-Water Interface", Biochimica et Biophysica ACTA, vol. 1467, No. 1, Jul. 31, 2000, pp. 131-143.
C. Rousselle et al., "New Advances in the Transport of Doxorubicin Through the Blood-Brain Barrier by a Peptide Vector-Mediated Strategy", Molecular Pharmacology, vol. 57, No. 4, Apr. 2000, pp. 679-686.
P. M. Fischer et al., "Structure-Activity Relationship of Truncated and Substituted Analogues of the Intracellular Delivery Vector Penetratin", Journal of Peptide Research, Munksgaard International Publishers, vol. 55, No. 2 Feb. 2000, pp. 163-172.
E. G. Thorén, et al., "The Antennapedia Peptide Penetratin Translocates Across Lipid Bilayers—The First Direct Observation", Febs. Letters, Elsevier Science Publishers, vol. 482, No. 3, Oct. 6, 2000, pp. 265-268.
Alain Prochiantz, "Getting Hydrophilic Compounds Into Cells: Lessons From Homeopeptides", Current Opinion in Neurobiology, vol. 6, No. 5, Oct. 1, 1996.
E. A. Jaeger, "Small Synthetic Peptides Homologous to Segments of Occludin Impair Tight Junction Resealing in a $Ca^{+2}$-Switch Assay in A6 Cell Monolayers", Molecular Biology of the Cell, vol. 8, Suppl., Nov. 1997, p. 205A, Abridged No. 1189 & 37th Annual Meeting of the American Society for Cell Biology, Washington, D.C., USA, Dec. 13-17, 1997.

(Continued)

*Primary Examiner* — Wu-Cheng Winston Shen
(74) *Attorney, Agent, or Firm* — Morgan, Lewis & Bockius LLP (57) ABSTRACT

The invention concerns peptide vectors, comprising a transduction domain, and a nuclear export sequence, for carrying a molecule of interest through an epithelium with tight junctions, such as the blood-brain barrier.

7 Claims, 5 Drawing Sheets

OTHER PUBLICATIONS

M. Dathe et al., Peptide Helicity and Membrane Surface Charge Modulate the Balance of Electrostatic and Hydrophobic Interactions with Lipid Bilayers and Biological Membranes:, Biochemistry, 1996, vol. 35, No. 38, pp. 12612-12622.

J. Oehlke et al., "Rapid Translocation of Amphipathic α-Helical and β-Sheet-Forming Peptides Through Plasma Membrances of Endothelial Cells", Pept. Sci.: Present Future, Proc. Int. Pept. Symp., 1st, 1999, vol. Meeting Date 1997, 782-78.

A. Scheller et al., "Structural Requirements for Cellular Uptake of α-Helical Amphipathic Peptides", J. Pept. Sci., 1999, vol. 5, No. 4, pp. 185-194.

* cited by examiner

Control intravenous injection     Intravenous injection of NES-Pen

Figure 6

CARRIER VECTORS THROUGH AN EPITHELIUM WITH TIGHT JUNCTIONS

The present invention relates to novel vectors capable of transporting active molecules across the blood-brain barrier and, more generally, across epithelia forming tight barriers between two compartments.

The function of the blood-brain barrier (BBB) is to keep the brain from experiencing variations in blood composition, and to protect the nerve cells against potentially toxic substances. It lies at the level of the endothelium of the capillary vessels which irrigate the central nervous system. This endothelium has particular properties which differentiate it from that of the other capillaries of the body. It lacks the pores which are found in a large number of other capillaries. In addition, the cells which constitute it are tightly joined to one another. These "tight junctions" also have a high electrical resistance (of the order of 1000 ohms/cm$^2$) and therefore constitute an effective obstacle even against passive diffusion of ions.

The blood-brain barrier therefore constitutes a very selective filter which only allows a small number of substances to pass naturally. These are mainly:
 low molecular weight lipophilic molecules, which can cross the blood-brain barrier by passive diffusion;
 low molecular weight hydrophilic molecules, constituting nutrients which are essential for the function of nerve cells (in particular sugars, amino acids, neuropeptides, vitamins, etc.). These molecules cross the blood-brain barrier via specific transporters;
 high molecular weight molecules (for example polypeptide hormones), which cross the blood-brain barrier after binding to their specific receptors present at the surface of the endothelial cells.

The impermeability of the blood-brain barrier constitutes a major obstacle to the penetration of many medicinal products into the brain.

In order to remedy this, several approaches have been proposed:
1) Direct administration of the desired molecule in the central nervous system, by intrathecal injection or infusion. This method has the drawback of being extremely invasive and delicate to implement. A related approach consists of grafting, into the central nervous system, cells which have been genetically modified so as to produce the substance to be administered, thus acting like "minipumps" to deliver said substance in situ. Despite its potential advantage, this approach will remain limited to drugs which can be synthesized and secreted by a cell.
2) Momentary opening of the BBB, in general caused by osmotic shock or by the action of certain substances (for example bradykinin or angiotensin), which transiently open the tight junctions by interacting with the extracellular domain of some of their components. This approach has the drawback of being nonselective and of allowing many other molecules present in the blood to cross at the same time as the molecule to be transported.
3) Use of the natural mechanisms for crossing the blood-brain barrier. Passive diffusion can, however, only be used for low molecular weight substances which are lipophilic, or which can be made lipophilic without, however, modifying their pharmacological properties. The specific transporters can be used only for molecules with a structure sufficiently close to that of the substances naturally transported by them. In the case of specific receptors, it has been proposed to conjugate natural ligands for these receptors with the molecule to be transported; a major drawback of this approach lies in the biological activity specific to these ligends, which can cause more or less unpleasant side effects.

Recently, it has been proposed to use transducing peptides as vectors for transport across the blood-brain barrier. Transducing peptides are peptides comprising a sequence referred to as "transduction domain" which imparts to them the ability to penetrate into a living cell, independently of the presence of specific transporters or receptors.

Review articles concerning transducing peptides have recently been published by LIDGREN et al., [TiPS, 21, 99-102, (2000)]; SCHWARZE and DOWDY [TIPS, 21, 45-48, (2000)]; SCHWARZE et al. [Trends Cell. Biol., 10, 290-295, (2000)]; PROCHIANTZ [Current Opinion in Cell Biology, 12, 400-406, (2000)].

By way of examples of transducing peptides, mention will in particular be made of:
 penetrating, which are peptides derived from the third helix of a homeodomain; peptides of the penetratin family are described, for example, in the publications by JOLIOT et al. [Proc. Natl. Acad. Sci. USA, 88, 1864-1868, (1991)]; DEROSSI et al. [J. Biol. Chem., 269, 14, 10444-10450, (1994)]; BRUGIDOU et al. [Biophys. Biochem. Res. Com., 214, 685-693, (1995)], and also in U.S. Pat. No. 5,888,762, U.S. Pat. No. 6,080,724, or PCT application WO/00/01417;
 peptides derived from the HIV1 Tat protein, and in particular from fragment 48-60 of said protein; such peptides are described, for example, by FAWELL et al. [Proc. Natl. Acad. Sci. USA., 91, 664-668, (1994)] or by VIVES et al. [J. Biol. Chem., 272, 16010-16017, (1997)];
 peptides derived from the HSV VP22 protein; such peptides are described, for example, by ELLIOTT and O'HARE [Cell, 88, 223-233, (1997)];
 peptides derived from a signal sequence, optionally conjugated to a nuclear localization sequence; such peptides are described, for example, by LIN et al. [J. Biol. Chem., 270, 14255-14258, (1995); J. Biol. Chem., 271, 5305-5308, (1996)], LIU et al. [Proc. Natl. Acad. Sci. USA, 93, 11819-11824, (1996)], MORRIS et al. [Nucleic Acids Res., 25, 2730-2736, (1997)], CHALOIN et al. [Biochemistry, 36, 11179-11187, (1997); Biochem. Biophys. Res. Commun., 243, 601-608, (1998)], ZHANG et al. [Proc. Natl. Acad. Sci. USA, 95, 9184-9189, (1998)];
 transportans, which are derived from fusion between a portion of a neuropeptide, galanin, and a wasp venom peptide [POOGA et al., FASEB J., 12, 67-77, (1998); Ann. New York Acad. Sci., 863, 450-453, (1998)].

SCHWARZE et al. [Science, 285, 1569-1572, (1999)] have observed that β-galactosidase coupled to a transduction domain of the Tat protein can be detected, after intraperitoneal administration, in all the tissues of the body, including the brain.

ROUSSELLE et al. [Mol. Pharmacol, 57, 679-686, (2000)] also report that coupling doxorubicin with D-penetratin or the SynB1 peptide increases its passage across the blood-brain barrier.

Although the use of transducing peptides appears to increase passage across the blood-brain barrier, this nevertheless remains very low.

Furthermore, in prior studies, the inventors' team has demonstrated, in the homeodomain protein Engrailed, the existence of a nuclear export sequence which contributes to the exit of this protein from the nucleus and to its passage into a secretion compartment [JOLIOT et al., Curr Biol, 8, 856-863, (1998); MAIZEL et al., Development, 126, 3183-3190, (1999)]. This sequence differs from a conventional secretion sequence of the signal peptide type, in terms of its structure and its position in the molecule.

The inventors have therefore investigated whether this nuclear export sequence is functional outside the context of the whole Engrailed protein. With this aim, they have compared the properties of penetration and of intracellular distribution of a peptide comprising only a transduction domain (consisting of a penetratin, in this case the third helix of the pAntp peptide), and of a peptide (NES-Penet) comprising, besides this transduction domain, the nuclear export sequence of the Engrailed protein. They have noted that, after penetration into cells at 37° C., the peptide comprising only the transduction domain is located in the nucleus and, in a diffuse manner, in the cytoplasm, whereas the peptide also comprising the nuclear export sequence is mainly located in a vesicular compartment of the cytoplasm. After penetration into cells at 4° C., the peptide comprising only the transduction domain, and also that comprising in addition the nuclear export sequence, remain located in the nucleus. If the cells are then brought to 37° C., it is observed that the peptide comprising the transduction domain and the nuclear export sequence passes into the vesicular compartment, which reflects an energy-dependant nuclear export mechanism.

The inventors have also investigated whether the addition of the nuclear export sequence modifies the ability of the penetratin to interact with the vesicular compartment. With this aim, they incubated each of the 2 peptide with purified membrane fractions, and treated them with trypsin. They then observed that the peptide containing the transduction domain alone (penetratin) was almost completely degraded by the trypsin, whereas the peptide comprising the transduction domain and the nuclear export sequence (NES-Penet) was protected against the action of the trypsin. The same fractionation and protection experiment was carried out after internalization by living cells; degradation of the penetratin and protection of the NES-Penet peptide were also observed. The fact that the penetratin incubated with the membranes alone is not protected suggests that the role of the nuclear export sequence is not limited to the exiting from the nucleus, but that it also allows access of the peptide to an intracisternal compartment, and accumulation thereof in said compartment.

In order to determine whether the passage into the vesicular compartment could result in effective externalization of the peptide, and whether this externalization was capable of facilitating passage across an epithelium with tight junctions, the inventors used an experimental model consisting of 2 compartments separated by a microporous membrane covered with a layer of cells, reproducing an epithelium with tight junctions. One of the compartments is in contact with the apical pole of the cells, and the other with their basolateral pole. They thus noted that, when the penetratin peptide comprising only the transduction domain is added to the basolateral compartment, entry of this peptide into the cells is observed, as is a small amount of passage to the apical compartment. When the same peptide is added to the apical compartment, it also enters the cells; on the other hand, no passage to the basolateral compartment is observed.

The same experiments were carried out in the case of the NES-Penet peptide; the passage from the basolateral compartment to the apical compartment is very greatly increased, whereas the passage from the apical compartment to the basolateral compartment remains slight or nonexistent.

In addition, the inventors compared the entry and the exit of the penetratin and NES-Penet peptides placed in one or other of the two compartments, at 4° C. and at 37° C. They observed that the entry of one or other of these peptides occurs at 4° C. as at 37° C., but that the exit of NES-Penet is blocked at 4° C., which confirms that the mechanisms of entry and of exit are different.

It therefore appears that combining a nuclear export sequence with a transduction domain makes it possible to increase the efficiency of transport across an epithelium with tight junctions, in the basolateral/apical direction.

A subject of the present invention is the use of a peptide comprising at least one amino acid sequence constituting a transduction domain and an amino acid sequence constituting a nuclear export sequence, as a vector for transporting a molecule of interest across an epithelium with tight junctions, in particular across the blood-brain barrier and the choroid plexus.

In particular, a subject of the present invention is the use of at least one amino acid sequence constituting a transduction domain and of at least one amino acid sequence constituting a nuclear export sequence, for producing a vector intended to transport a molecule of diagnostic or therapeutic interest across an epithelium with tight junctions, in particular across the blood-brain barrier and the choroid plexus.

Transduction domains which can be used to implement the present invention are known in themselves and are in particular described in the publications of the prior art mentioned above.

Said transduction domain may or may not comprise a nuclear localization sequence (NLS).

"Nuclear localization sequence" is defined as a sequence which, when it is present in a transduction domain, allows access thereof to the nucleus after its entry into the cell.

By way of nonlimiting examples of peptides constituting transduction domains comprising a nuclear localization sequence, mention will in particular be made of:
  (i) peptides comprising fragment 48-60 of the HIV1 Tat protein;
  (ii) the fusion between the NLS of NFkB and the signal peptide of K-FGF;
  (iii) the fusion between NLS of the SV40 T antigen and the signal peptide of K-FGF;
  (iv) penetrating.

By way of nonlimiting examples of peptides constituting transduction domains not comprising a nuclear localization sequence, mention will in particular be made of:
  (i) the amphiphilic peptide KLALKLALKALKAALKLA (SEQ ID NO: 1);
  (ii) certain variants of penetratins [DEROSSI et al., J. Biol. Chem., 271, 18188-18193, (1996)].

When the transduction domain does not comprise a nuclear localization sequence, it may optionally, if desired, be combined with a heterologous nuclear localization sequence.

The expression "nuclear export sequence" (NES) is intended to mean any peptide sequence capable of imparting to a peptide comprising said sequence the ability to leave the cell nucleus and enter a secretion compartment.

Nuclear export sequences which are known in themselves can be used to implement the present invention. 3 types of nuclear export sequence have been described at the current time (for review cf., for example, NAKIELNY and DREYFUSS, Current Opinion in Cell Biology 9, 420-429, 1997): the "leucine-rich" nuclear export sequences, which are sequences of approximately 10 amino acids comprising a large proportion of aliphatic hydrophobic amino acids (leucine or isoleucine, and also valine or alanine), which are present in a large number of proteins, included among which are the homeodomain proteins; the M9 sequence of hnRNP A1 [MICHAEL et al., Cell, 83, 415-422, (1995)]; the KNS (for: "hnRNP K nuclear shuttling domain") sequence of hnRNP K [MICHAEL et al., EMBO J., 16, 3587-3598, (1997)].

According to a preferred embodiment of the present invention, use will be made of a leucine-rich nuclear export sequence, and in particular a nuclear export sequence of a homeodomain protein. Nuclear export sequences of homeodomain proteins which can in particular be used to implement the present invention are sequences of approximately 10 to 15 amino acids, located, in these proteins, at the N-terminal end of the 3rd helix, or partially covering it. Use may, by way of example, be made of a nuclear export sequence of the "Engrailed" protein, comprising at least the sequence (1-letter code) AQELGLNESQI (SEQ ID NO: 2), and advantageously at least the sequence (1-letter code) SLAQELGLNERQIKI (SEQ ID NO: 3).

The nuclear export sequence and the transduction domain can be directly adjacent, separated by another amino acid sequence, or at least partially overlapping.

The present invention can be used to transport across an epithelium with tight junctions, and in particular across the blood-brain barrier, any molecule of diagnostic or therapeutic interest which can be transported into a living cell by a transducing peptide, including a homeodomain protein. It can thus in particular be used to transport nucleic acids, polypeptides, peptide/nucleic acids, or nucleotide analogs used in particular as antineoplastic agents.

For the implementation of the present invention, the molecule to be transported can be attached anywhere on the vector peptide, on condition that this attachment does not modify the functionalities of the transduction domain or of the nuclear export sequence. Said molecule can, for example, be attached to the N-terminal end, to the C-terminal end or to the interior of said peptide, for example between the transduction domain and the nuclear export sequence.

The conjugation between the molecule to be transported and the vector peptide can be carried out directly, or via a linker, using the same methods as those used for conjugation to a transducing peptide. Various suitable methods are known in themselves, and are in particular described in the publications of the prior art mentioned above.

The present invention will be more clearly understood from the further description which follows, which refers to nonlimiting examples illustrating the passage of a peptide comprising a transduction domain and a nuclear export domain across an epithelium with tight junctions.

EXAMPLE 1

Intracellular Localization of a Peptide Comprising the Transduction Domain of the pANTP Peptide and the Nuclear Export Sequence of the Engrailed Protein The following biotinylated peptide is synthesized:
Biot-QSLAQELGLNERQIKIWFQNRRMKWKK-COOH (SEQ ID NO: 4).

This peptide (hereinafter referred to as NES-Penet) comprises, with a partial overlap, a sequence:
QSLAQELGLNERQIKI (SEQ ID NO: 5)
containing the nuclear export sequence of the Engrailed protein,
and a penetratin sequence:
RQIKIWFQNRRMKWKK (SEQ ID NO: 6)
consisting of helix 3 of the pAntp peptide (homeodomain of the drosophila Antennapedia protein).

It is also labeled at its N-terminal end with a biotin attached via an aminopentanoic arm.

As a control, the biotinylated peptide:
Biot-RQIKIWFQNRRMKWKK-COOH (hereinafter referred to as Penet-1)
comprising only the penetratin sequence was also synthesized.

Each of the 2 peptides was incubated, at a concentration of 10 µM, with rat embryo brain cells (E17, $10^7$ cells/ml) in suspension, for 1 hour at 37° C.

The cells were lyzed and fractionated according to the following protocol:

The cells are lyzed in 200 µl of 10 mM Hepes buffer, 3 mM $MgCl_2$, pH 7, containing a cocktail of protease inhibitors. The lysis is carried out by pushing the cells back and forth through a G26 needle mounted on a 1 ml syringe, ten times.

After centrifugation of the extracts (150 000 g for 1 hour, 40° C.) through a 0.25 M and 1.7 M discontinuous sucrose cushion, the nuclei are recovered in the pellet and the membrane fraction is recovered at the 0.25 M/1.7 M interface.

A portion of each of these fractions was then treated with trypsin according to the following protocol: incubation in phosphate buffer (PBS) for 1 hour, 4° C., in the presence of 100 µg/ml trypsin; the reaction is stopped by adding 10% (vol/vol) trichloroacetic acid (TCA) at 100° C. for 5 min.

The fractions, untreated or treated with trypsin, were then analyzed by electrophoresis under denaturing conditions on a 22% polyacrylamide gel in the presence of SDS.

The Penet-1 and NES-Penet peptides were revealed with streptavidin-peroxidase according to the protocol described by DEROSSI et al. [J. Biol. Chem., 271, 18188-18193, (1996)].

Figure 1:
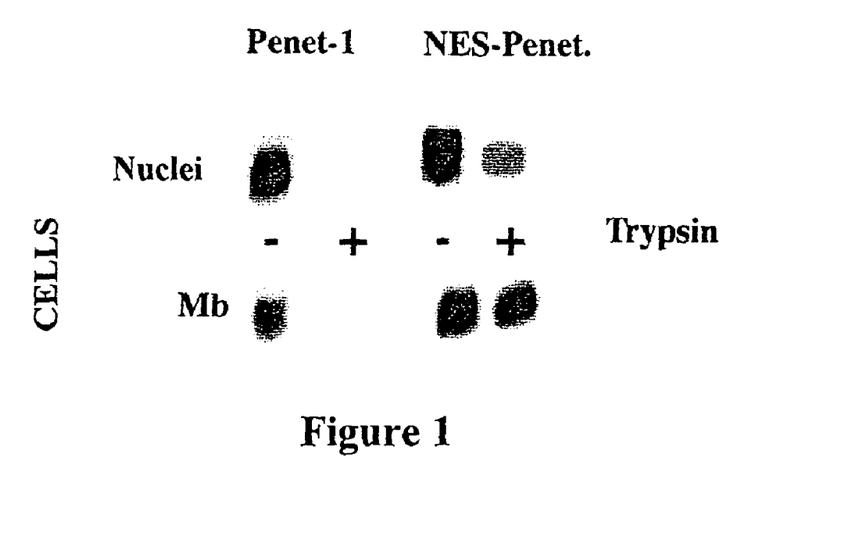
FIG. 1 shows Penet-1 and NES-Penet peptides revealed with steptavidin-peroxidase.

The results are given in FIG. 1.

In the absence of treatment with trypsin (−) it is observed that the Penet-1 and NES-Penet peptides associate with the nuclear fraction (nuclei) and with the membrane fraction (Mb).

The treatment with trypsin (+) induces degradation of the Penet-1 peptide in the nuclear fraction and the membrane fraction. On the other hand, in the case of the NES-Penet peptide, no degradation is observed in the membrane fraction, and partial protection against degradation is observed in the nuclear fraction. This protection probably reflects a slight contamination of this fraction with perinuclear membranes.

In a 2nd series of experiments, the cells in culture were lyzed and the membrane fractions were purified according to the protocol described above, without prior incubation with the peptides.

Each of the 2 peptides Penet-1 and NES-Penet was incubated, at a concentration of 10 μM, with the preparation of membrane fractions derived from $10^7$ neurons (as above), for 1 hour at 37° C., and then treated with trypsin according to the protocol described above.

After incubation, the peptide/membrane preparation mixture was treated with trypsin according to the protocol described above.

In parallel, each of the 2 peptides Penet-1 and NES-Penet was treated with trypsin, under the same conditions, without prior incubation with the membrane preparation.

The trypsin lysates were analyzed by electrophoresis as described above.

Figure 2:
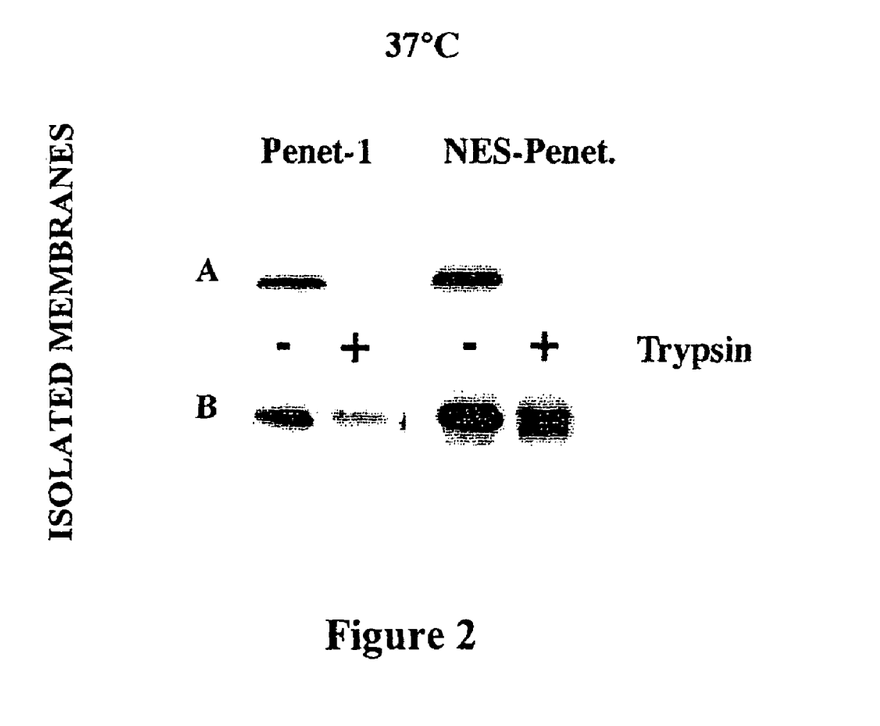
FIG. 2 shows trypsin lysates analyzed by electrophoresis.

The results are given in FIG. 2.

In the absence of incubation with the membrane preparation (A), total degradation of the Penet-1 and NES-Penet peptides is observed after treatment with trypsin (+).

After incubation with the membrane preparation (B), partial protection of the Penet-1 peptide (it being possible for the amount of protected peptide to be evaluated at less than 30%) and virtually total protection of the NES-Penet peptide are observed after treatment with trypsin (+).

These results show that, independently of the presence of nuclei, the nuclear export sequence promotes access of the peptide to an intramembrane compartment, and/or the maintenance thereof in this compartment.

EXAMPLE 2

Figure 3:
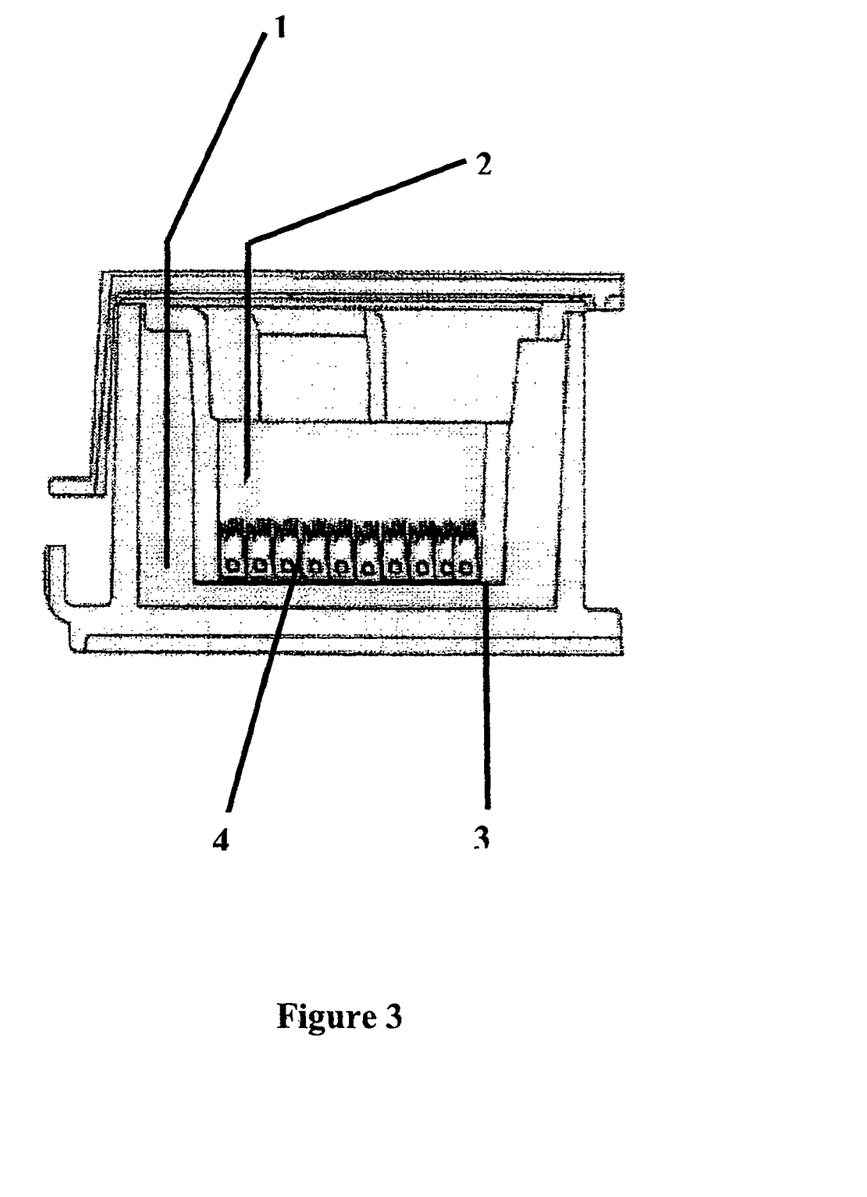
FIG. 3 shows the device for evaluating the passage of Penet-1 and NES-Penet peptides across an epithelium with tight junctions.

Passage of a Peptide Comprising the Transduction Domain of the pANTP Peptide and the Nuclear Export Sequence of the Engrailed Protein Across an Epithelium with Tight Junctions The passage of the Penet and NES-Penet peptides across an epithelium with tight junctions was evaluated using the device (TRANSWELL system, CORNING-COSTAR) represented in FIG. 3.

This device comprises two compartments (1, 2) separated by a microporous polyester membrane (3) on which an epithelium (4) consisting of MDCK (Madin-Darby Canine Kidney) cells has been established. The cells are seeded and grow to confluence.

The compartment (1) in contact with the microporous membrane and the basolateral pole of the cells is referred to as the basolateral compartment. The compartment (2), in contact with the apical pole of the cells, is referred to as the apical compartment.

Each of the compartments is filled with medium consisting of the following: Minimum Essential Medium with Earle Salt (MEM), 2 mM glutamine, 2 mM Hepes, pH 7, 5 U/ml penicillin, 5 μg/ml streptomycin, supplemented with a mixture of protease inhibitors.

For each experiment, the integrity of the tight junctions is controlled by measuring the resistance between the two compartments (R>2000Ω/cm²).

Moreover, the tightness of the epithelium was also verified by adding triturated inulin ($6.5 \times 10^5$ cpm/compartment), either to the apical compartment or to the basolateral compartment, and measuring the radioactivity in the other compartment 180 minutes later. Under these conditions, no passage of the triturated inulin was observed in the apical/basolateral direction nor in the basolateral/apical direction.

The biotinylated Penet-1 peptide or the biotinylated NES-Penet peptide, each used at a concentration of 10 μM, is placed either in the apical compartment or in the basolateral compartment. The other compartment contains streptavidin, at a concentration of 10 μM, allowing capture of the biotinylated peptide. After incubation for 30 minutes at 37° C., or at 4° C., the medium in the starting compartment and the medium in the end compartment are sampled.

The peptides are precipitated by adding 10% trichloroacetic acid (TCA), and taken up in boiling Laemmli medium. The cells are rinsed in a 0.5 M NaCl solution and then lyzed in boiling Laemmli medium. The presence of the Penet-1 or NES-Penet peptides in the starting compartment, in the end compartment, or inside the cells, is detected by revelation with streptavidin-peroxidase as indicated in Example 1 above.

Figure 4:
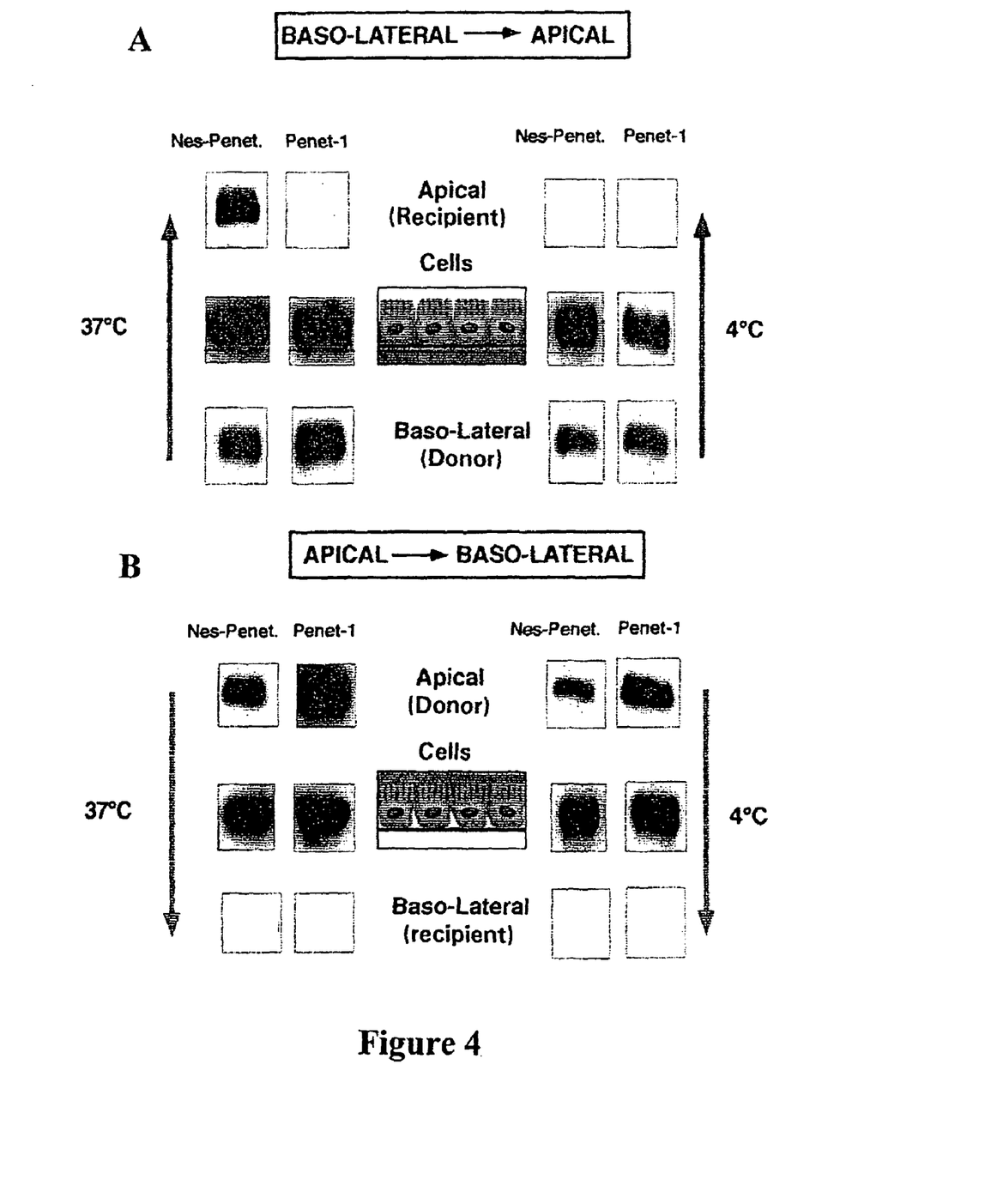
FIG. 4A represents the electrophoretic analysis of the NES-Penet and Penet-1 peptides when the starting compartment is the basolateral compartment.
FIG. 4B represents the electrophoretic analysis of the NES-Penet and Penet-1 peptides when the starting compartment is the apical compartment.

The results are illustrated in FIGS. 4A and 4B.

FIG. 4A represents the electrophoretic analysis of the NES-Penet and Penet-1 peptides after incubation for 30 minutes, when the starting compartment is the basolateral compartment. At 37° C. (left panel), penetration of the 2 peptides into the cells and a very small amount of passage of the Penet-1 peptide into the apical compartment are observed; on the other hand, the passage of the NES-Penet peptide into the apical compartment is much greater. It is also observed that the passage is not accompanied by any degradation of the peptide. At 4° C. (right panel), penetration of the 2 peptides into the cells is also observed; on the other hand, neither of the 2 peptides passes into the apical compartment.

FIG. 4B represents the electrophoretic analysis of the NES-Penet and Penet-1 peptides after incubation for 30 minutes, when the starting compartment is the apical compartment. At 37° C., as at 4° C., penetration of the 2 peptides into the cells is observed, but no passage into the basolateral compartment is observed.

When the same experiments are carried out in the presence of calf serum, at a concentration of 10% in the starting compartment, identical results are observed, which shows that the passage is not blocked by serum components.

These results demonstrate that the two peptides can be internalized by the two faces of the epithelium, but that the presence of the nuclear export sequence substantially increases the passage of the NES-Penet peptide across the epithelium, and that this passage is polarized and occurs only in the basolateral/apical direction.

In addition, the temperature has no effect on the entry (it occurs at 4° C. and 37° C.), whereas the exit is temperature dependant (it is blocked at 4° C.), which shows that these 2 phenomena correspond to different processes.

In another series of experiments, the effect of brefeldin A (BFA), which blocks protein secretion involving the Golgi apparatus, on the passage of the NES-Penet peptide was studied.

The biotinylated NES-Penet peptide (10 μM) was incubated in the basolateral compartment, under the conditions described above, for one hour at 4° C. or at 37° C., in the presence or absence of brefeldin A (10 μM)

At the end of the incubation, the contents of the basolateral compartment and of the apical compartment, and that of the cells, were analyzed as described above in order to detect the presence of the NES-Penet peptide.

Figure 5:
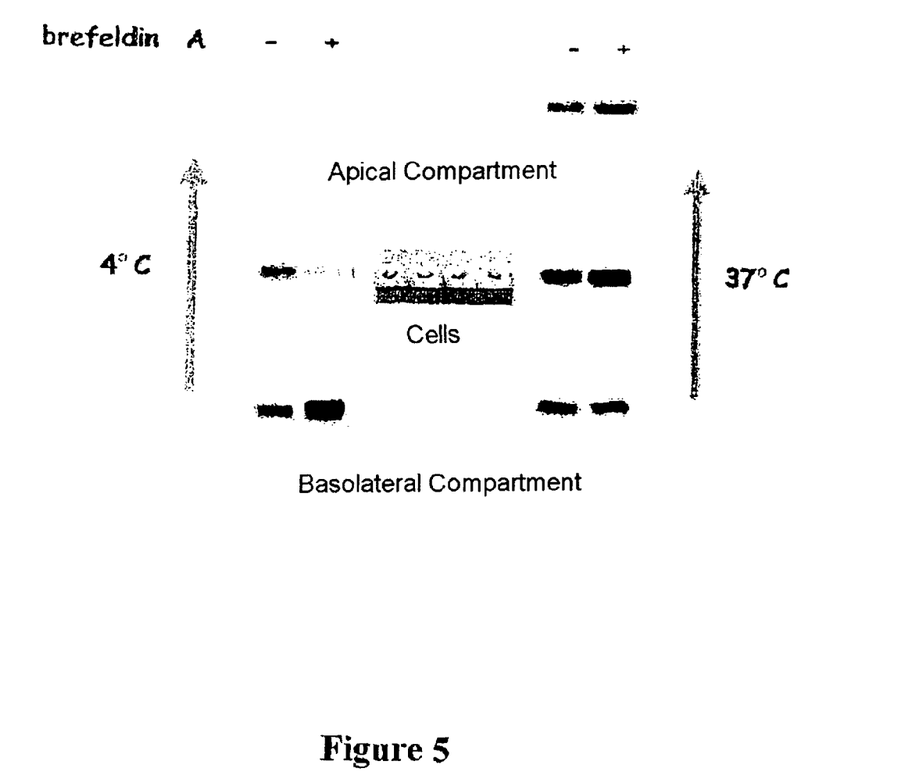
FIG. 5 shows analysis of the contents of the basolateral compartment and the apical compartment after incubation.

The results are illustrated in FIG. 5.

These results confirm that the NES-Penet peptide enters at 4° C. (left panels) but does not re-exit at this temperature, whether in the presence (+) or absence (−) of brefeldin A. On the other hand, at 37° C. (right panels), the exit of the NES-Penet peptide is observed in the presence (+) or absence (−) of brefeldin A.

These results show that the crossing of the epithelium by the NES-Penet peptide does not involve passing via the Golgi apparatus.

EXAMPLE 3

In Vivo Passage of NES-Penet Across the Blood-Brain Barrier

The biotinylated NES-Penet peptide (50 μg/50 μl of PBS) or PBS (50 μl) are injected into the tail vein of a mouse; this mouse is sacrificed one hour after the injection. The brain is removed and fixed with 4% para-formaldehyde, and cryoprotected by immersion overnight at 4° C. in a solution of PBS containing 20% sucrose. Frontal sections of the brain (10 μM thick) are then cut on a cryostat. The peptide is then revealed on these sections using a streptavidin-fluorescein complex, and the fluorescence is analyzed by confocal microscopy.

Figure 6:
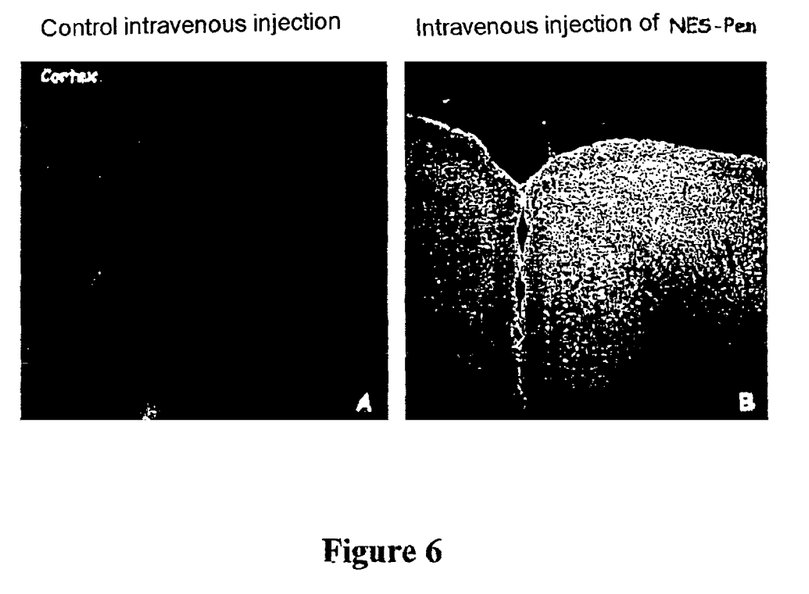
FIG. 6 shows that the biotinylated NES-Penet peptide crosses the blood-brain barrier and reaches the cortex and the subcortical regions.

The results are illustrated in FIG. 6 (A: PBS; B: NES-Penet peptide). These results show that the biotinylated NES-Penet peptide crosses the blood-brain barrier in a very significant manner, and reaches the cortex and the subcortical regions.

EXAMPLE 4

Influence of the Nuclear Export Sequence on the Subcellular Localization and the Transepithelial Passage of Peptides containing Transduction Domains of Various Types The intracellular localization, and the passage across an epithelium with tight junctions, of the NES-Penet peptide described above were compared with those of a peptide, hereinafter referred to as NES-Pen3P, comprising the nuclear export sequence of the Engrailed protein described in Example 1, and a penetratin sequence (hereinafter referred to as Pen3P) derived from helix 3 of the pAntp peptide by substitution of the Ile, Gln and Lys residues located, respectively, at positions 45, 50 and 55 of the Antp homeodomain, with 3 proline residues. The Pen3P peptide penetrates into the cells, but is not addressed to the nucleus. The Pen3P sequence initially described in DEROSSI et al. [J. Biol. Chem., 271, 30, 18188-18193, (1996)] is RQPKIWFPNRRKPWKK (SEQ ID NO: 7).

The sequence of the biotinylated NES-Pen3P peptide is as follows:
Biot-QSLAQELGLNERQPKIWFPNRRKPWKK-COOH (SEQ ID NO: 8)

The biotinylated Penet, NES-Penet, Pen3P and NES-Pen3P peptides are added, at a concentration of 100 μM, to cultures of MDCK cells. After incubation for two hours at 4° C., the cells are rinsed with medium precooled to 4° C. containing NaCl at a concentration of 0.5 M; they are then immediately fixed with a 4% paraformaldehyde solution (5 minutes at ambient temperature) or, alternatively, they undergo a chase at 37° C. with peptide-free culture medium for 30 minutes before being fixed with paraformaldehyde. They are then permeabilized for 5 min at −20° C. with methanol, and preincubated for one hour in PBS containing 5% of fetal calf serum. The peptides are revealed using a streptavidin-fluorescein complex. The fluorescence is then analyzed by confocal microscopy.

The Penet peptide enters at 4° C.; at this temperature, diffuse cytoplasmic labeling, and more intense nuclear labeling, which becomes accentuated after transfer to 37° C., are observed.

The NES-Penet peptide enters at 4° C.; at this temperature, diffuse labeling, without notable cytoplasmic or nuclear localization, is observed. After transfer to 37° C., strong association of the labeling with intracytoplasmic vesicles, which probably correspond to a non-post-golgian secretion compartment (cf. Example 2), is observed.

The Pen3P peptide enters at 4° C.; as in the case of the NES-Penet peptide, diffuse cytoplasmic and nuclear labeling is observed at this temperature. On the other hand, unlike the NES-Penet peptide, this labeling is not modified at 37° C.

The NES-Pen3P peptide enters at 4° C.; as in the case of the NES-Penet peptide, diffuse cytoplasmic and nuclear labeling is observed at this temperature. At 37° C., strong association of the labeling with intra-cytoplasmic vesicles, similar to that observed for NES-Penet, is observed.

Furthermore, the passage of the peptides across an epithelium with tight junctions was evaluated using the device described in Example 2 above.

The biotinylated peptides (10 μM) are incubated in the basolateral compartment, under the conditions described above, for 30 minutes at 370° C. At the end of the incubation, the contents of the basolateral compartment and of the apical compartment, and that of the cells, are analyzed as described in Example 2.

Penetration of the Pen3P and NES-Pen3P peptides into the cells, and a very slight passage of the Penet3P peptide into the apical compartment, are observed; on the other hand, the passage of the NES-Penet3P peptide into the apical compartment is much greater.

These results show that the addressing to a secretion compartment and the passage across an epithelium with tight junctions do not require prior nuclear addressing of the peptides.

The invention claimed is:

1. A method of transporting and accumulating a molecule of diagnostic or therapeutic interest across an epithelium with tight junctions and accumulating said molecule of diagnostic or therapeutic interest on the apical side of said epithelium with tight junctions in vivo comprising contacting a transducing peptide that is operably attached to the molecule of diagnostic or therapeutic interest with the basolateral side of the epithelium, wherein the transducing peptide comprises at least one amino acid sequence constituting a transduction domain from the third helix of a homeodomain protein and an amino acid sequence constituting a nuclear export sequence, and wherein the molecule of diagnostic or therapeutic interest attached to the transducing peptide is transported from the basolateral extracellular side of said epithelium through the epithelial cells to accumulate on the apical extracellular side.

2. The method of claim 1 wherein the transduction domain and the nuclear export sequence are capable of transporting the molecule of diagnostic or therapeutic interest across the blood-brain barrier or the choroid plexus.

3. The method of claim 1 wherein the nuclear export sequence is a nuclear export sequence of an engrailed homeodomain protein.

4. The method of claim 1 wherein the nuclear export domain comprises at least the peptide sequence AQELGLNESQI (SEQ ID NO: 2).

5. The method of claim 1 wherein the nuclear export sequence comprises at least the peptide sequence SLAQELGLNERQIKI (SEQ ID NO: 3).

6. The method of claim 2, wherein the molecule of diagnostic or therapeutic interest is selected from the group consisting of nucleic acids, polypeptides, peptide/nucleic acids, and nucleotide analogs.

7. The method of claim 1, wherein the transduction domain is from the third helix of pAntp homeodomain protein.

* * * * *

SEQUENCE LISTING

```
<160> NUMBER OF SEQ ID NOS: 8

<210> SEQ ID NO 1
<211> LENGTH: 18
<212> TYPE: PRT
<213> ORGANISM: Artificial
<220> FEATURE:
<223> OTHER INFORMATION: penetratin sequence for transport vectors

<400> SEQUENCE: 1

Lys Leu Ala Leu Lys Leu Ala Leu Lys Ala Leu Lys Ala Ala Leu Lys
1               5                   10                  15

Leu Ala
```

-continued

```
<210> SEQ ID NO 2
<211> LENGTH: 11
<212> TYPE: PRT
<213> ORGANISM: Artificial
<220> FEATURE:
<223> OTHER INFORMATION: nuclear export sequence for transport vectors

<400> SEQUENCE: 2

Ala Gln Glu Leu Gly Leu Asn Glu Ser Gln Ile
1               5                   10

<210> SEQ ID NO 3
<211> LENGTH: 15
<212> TYPE: PRT
<213> ORGANISM: Artificial
<220> FEATURE:
<223> OTHER INFORMATION: nuclear export sequence for transport vectors

<400> SEQUENCE: 3

Ser Leu Ala Gln Glu Leu Gly Leu Asn Glu Arg Gln Ile Lys Ile
1               5                   10                  15

<210> SEQ ID NO 4
<211> LENGTH: 27
<212> TYPE: PRT
<213> ORGANISM: Artificial
<220> FEATURE:
<223> OTHER INFORMATION: nuclear export and penetratin sequence for
      transport vectors

<400> SEQUENCE: 4

Gln Ser Leu Ala Gln Glu Leu Gly Leu Asn Glu Arg Gln Ile Lys Ile
1               5                   10                  15

Trp Phe Gln Asn Arg Arg Met Lys Trp Lys Lys
            20                  25

<210> SEQ ID NO 5
<211> LENGTH: 16
<212> TYPE: PRT
<213> ORGANISM: Artificial
<220> FEATURE:
<223> OTHER INFORMATION: nuclear export sequence for transport vectors

<400> SEQUENCE: 5

Gln Ser Leu Ala Gln Glu Leu Gly Leu Asn Glu Arg Gln Ile Lys Ile
1               5                   10                  15

<210> SEQ ID NO 6
<211> LENGTH: 16
<212> TYPE: PRT
<213> ORGANISM: Artificial
<220> FEATURE:
<223> OTHER INFORMATION: penetratin sequence for transport vectors

<400> SEQUENCE: 6

Arg Gln Ile Lys Ile Trp Phe Gln Asn Arg Arg Met Lys Trp Lys Lys
1               5                   10                  15

<210> SEQ ID NO 7
<211> LENGTH: 16
<212> TYPE: PRT
<213> ORGANISM: Artificial
<220> FEATURE:
<223> OTHER INFORMATION: penetratin sequence for transport vectors

<400> SEQUENCE: 7

Arg Gln Pro Lys Ile Trp Phe Pro Asn Arg Arg Lys Pro Trp Lys Lys
```

-continued

```
<210> SEQ ID NO 8
<211> LENGTH: 27
<212> TYPE: PRT
<213> ORGANISM: Artificial
<220> FEATURE:
<223> OTHER INFORMATION: nuclear export and penetratin sequence for
      transport vectors

<400> SEQUENCE: 8

Gln Ser Leu Ala Gln Glu Leu Gly Leu Asn Glu Arg Gln Pro Lys Ile
1               5                   10                  15

Trp Phe Pro Asn Arg Arg Lys Pro Trp Lys Lys
            20                  25
```